(12) United States Patent
Beller et al.

(10) Patent No.: US 9,375,248 B2
(45) Date of Patent: Jun. 28, 2016

(54) ELECTROSURGICAL HF GENERATOR

(75) Inventors: Juergen Beller, Gomaringen (DE); Ralf Klein, Rottenburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1076 days.

(21) Appl. No.: 13/121,435

(22) PCT Filed: Aug. 12, 2009

(86) PCT No.: PCT/EP2009/005856
§ 371 (c)(1),
(2), (4) Date: Mar. 29, 2011

(87) PCT Pub. No.: WO2010/037446
PCT Pub. Date: Apr. 8, 2010

(65) Prior Publication Data
US 2011/0178517 A1    Jul. 21, 2011

(30) Foreign Application Priority Data

Oct. 1, 2008 (DE) .......................... 10 2008 050 032
Nov. 3, 2008 (DE) .......................... 10 2008 054 351

(51) Int. Cl.
*A61B 18/14* (2006.01)
*A61B 18/12* (2006.01)
*A61B 18/16* (2006.01)

(52) U.S. Cl.
CPC ......... *A61B 18/1206* (2013.01); *A61B 18/1442* (2013.01); *A61B 18/16* (2013.01); *A61B 2018/124* (2013.01); *A61B 2018/165* (2013.01)

(58) Field of Classification Search
CPC ........... A61B 18/085; A61B 18/14442; A61B 18/1445; A61B 18/1447; A61B 18/12; A61B 2018/00827; A61B 2018/00898; A61B 2018/00916; A61B 2018/00875; A61B 2018/00985; A61B 2018/1442–2018/1462; A61B 2018/1467; A61B 2018/165; A61B 2018/162; A61B 2018/167; A61B 18/16
USPC ....................................... 606/20–52
See application file for complete search history.

(56) References Cited

U.S. PATENT DOCUMENTS

| 3,906,957 | A | * | 9/1975 | Weston | ............. A61B 17/2804 |
| | | | | | 24/562 |
| 4,184,492 | A | * | 1/1980 | Meinke et al. | .................. 606/35 |
| 4,754,757 | A | | 7/1988 | Feucht | |
| 5,472,442 | A | * | 12/1995 | Klicek | ............................. 606/42 |
| 5,562,720 | A | * | 10/1996 | Stern et al. | ...................... 607/98 |
| 5,766,165 | A | | 6/1998 | Gentelia et al. | |
| 5,836,942 | A | * | 11/1998 | Netherly et al. | ................. 606/32 |
| 5,885,277 | A | * | 3/1999 | Korth | ............................. 606/35 |

(Continued)

FOREIGN PATENT DOCUMENTS

| DE | 35 44 443 C2 | 2/1994 |
| DE | 1 03 51 818 A1 | 6/2005 |

(Continued)

*Primary Examiner* — Jaymi Della
(74) *Attorney, Agent, or Firm* — Blank Rome LLP

(57) ABSTRACT

An electrosurgical high frequency (HF) generator comprising a generator circuit that produces an HF current between an active electrode and at least one neutral electrode. During the cutting or coagulating of biological tissue, unwanted tissue heating due to the HF current can be reduced because the electrosurgical HF generator comprises at least one further auxiliary neutral electrode connected in parallel to the neutral electrode.

14 Claims, 2 Drawing Sheets

(56) References Cited

U.S. PATENT DOCUMENTS

| | | | |
|---|---|---|---|
| 5,957,961 A * | 9/1999 | Maguire et al. | 607/99 |
| 5,976,132 A * | 11/1999 | Morris | 606/49 |
| 6,569,160 B1 * | 5/2003 | Goldin et al. | 606/41 |
| 6,775,575 B2 * | 8/2004 | Bommannan et al. | 607/101 |
| 6,953,461 B2 * | 10/2005 | McClurken et al. | 606/51 |
| 7,052,492 B2 * | 5/2006 | Swanson et al. | 606/32 |
| 7,070,594 B2 * | 7/2006 | Sherman | 606/21 |
| 7,097,644 B2 * | 8/2006 | Long | 606/41 |
| 7,226,465 B1 * | 6/2007 | Farin | 606/205 |
| 7,229,307 B2 * | 6/2007 | Ehr et al. | 439/371 |
| 7,604,635 B2 * | 10/2009 | McClurken et al. | 606/51 |
| 2004/0092926 A1 * | 5/2004 | Hoey et al. | 606/34 |
| 2004/0097916 A1 | 5/2004 | Thompson et al. | |
| 2004/0193148 A1 * | 9/2004 | Wham et al. | 606/40 |
| 2005/0096681 A1 * | 5/2005 | Desinger | A61B 18/1402 606/45 |
| 2005/0101947 A1 | 5/2005 | Jarrard et al. | |
| 2005/0267469 A1 * | 12/2005 | Blocher | 606/46 |
| 2006/0047280 A1 * | 3/2006 | Goble et al. | 606/48 |
| 2006/0095031 A1 * | 5/2006 | Ormsby | 606/41 |
| 2006/0293649 A1 * | 12/2006 | Lorang et al. | 606/32 |
| 2007/0049916 A1 * | 3/2007 | Isaacson et al. | 606/32 |
| 2007/0073284 A1 * | 3/2007 | Sturm et al. | 606/35 |
| 2007/0167942 A1 * | 7/2007 | Rick | 606/35 |
| 2007/0222458 A1 * | 9/2007 | Eisele | A61B 18/16 324/633 |
| 2007/0225699 A1 * | 9/2007 | Goble et al. | 606/34 |
| 2008/0058792 A1 | 3/2008 | Falkenstein et al. | |

FOREIGN PATENT DOCUMENTS

| | | |
|---|---|---|
| EP | 0 694 291 A1 | 1/1996 |
| EP | 1 902 684 A1 | 3/2008 |
| JP | 57-180950 A | 11/1982 |
| JP | 58-86155 A | 5/1983 |
| JP | 62-155841 A | 7/1987 |
| JP | 9-503423 A | 4/1997 |
| JP | 2005-131403 A | 5/2005 |
| JP | 2008-73527 A | 4/2008 |
| WO | WO 95/25471 A2 | 9/1995 |
| WO | WO 2004/045436 A1 | 6/2004 |
| WO | WO 2005/110263 A2 | 11/2005 |
| WO | WO 2007/022864 A1 | 3/2007 |

* cited by examiner

ELECTROSURGICAL HF GENERATOR

CROSS-REFERENCE TO RELATED APPLICATIONS

This application is the U.S. national stage of International Application No. PCT/EP2009/005856, filed Aug. 12, 2009.

FIELD OF THE INVENTION

Embodiments of the invention relate to an electrosurgical high frequency (HF) generator for treating biological tissue.

BACKGROUND

Electrosurgical HF generators are used for treating biological tissue, particularly for cutting or coagulating biological tissue. For this purpose, a generator circuit is provided for generating an HF current, which flows between an active electrode and at least one neutral electrode, via a first current path through the tissue. Accordingly, the generator circuit comprises an active output and a neutral output.

In HF surgery, a distinction is made between the known monopolar and bipolar uses. In monopolar use, the active electrode is configured as an insulated hand-piece, which, for example, has an electrode tip guided by a surgeon to the tissue regions to be treated. An HF current flows through the tissue to a neutral electrode, which contacts the tissue over a large area and is applied, for example, to the thigh of a patient. Such neutral electrodes usually have a contact area of approximately 1 $dm^2$ to 3 $dm^2$. Monopolar applications have the advantage of using a compact hand-piece, the electrode tip of which can also be applied to tissue sites that are difficult to reach. A disadvantage is that the HF current also flows to the neutral electrode through tissue not being treated. Particularly, if the cross-sectional area of the tissue along the current path is small, overheating and damage to regions of the tissue not being treated can occur. This can be counteracted with bipolar instruments. For bipolar instruments, the HF current flows between two closely adjacent electrodes e.g., bipolar coagulation forceps, and therefore exclusively through tissue situated between the clamping surfaces. With these instruments, however, poorly accessible tissue sites can often only be reached and treated with difficulty, or not at all.

SUMMARY

It is an object of the embodiments of the invention to provide an electrosurgical HF generator that enables treatment without the risk of damaging tissue not being treated, even for tissue sites that are difficult to reach.

This object is solved by an HF generator for treating (e.g., cutting or coagulating) biological tissue that generates an HF current by means of a generator circuit, said current flowing via a first current path between a first active electrode and at least one neutral electrode. Accordingly, the electrosurgical HF generator has an active output and a neutral output. The HF generator also has at least one auxiliary neutral electrode connected in parallel to the neutral electrode, so that part of the HF current flows through the tissue in a targeted way via at least one second current path. Because the entire HF current is distributed between at least two current paths, the current density in the current paths is reduced accordingly. As a consequence, the tissue along the current paths is only slightly heated, if at all. The risk of damage from overheating is correspondingly reduced.

Preferably, the electrosurgical HF generator comprises a measuring circuit that measures the ratio of the currents flowing through the neutral electrode and auxiliary neutral electrode. Alternatively or optionally, the measuring circuit can measure the HF current flowing through the neutral electrode and/or the auxiliary neutral electrode. The measuring circuit allows the determination of whether the HF current is distributed between the two current paths such that undesirable tissue damage is prevented. If the risk of undesirable tissue damage exists, an indication can be provided and/or the HF generator can switch off automatically. In most cases, the risk can be eliminated by repositioning e.g., the auxiliary neutral electrode.

The auxiliary neutral electrode can comprise, for example, at least one clamping surface of a preferably self-locking pair of grasping forceps. This is particularly advantageous if a part of the tissue is to be separated. The tissue part can be grasped with the grasping forceps so that the additional current path leads from the active electrode, through the tissue part to be separated, and to the clamping surface of the grasping forceps. In this way, damage to the tissue to be preserved is prevented due to the additional current path. If the part of the tissue to be separated is to be histologically examined, then said part of the tissue to be separated must not be damaged. This can be monitored by a measuring circuit, particularly one of the measuring circuits described herein.

Preferably, the two clamping surfaces of the grasping forceps are connected to the generator circuit. If both the clamping surfaces of the grasping forceps are connected in parallel to the neutral electrode, the contact surface of the auxiliary electrode is doubled; thus, reducing the loading on the tissue region contacted by the clamping surfaces.

The grasping forceps can be configured as bipolar grasping forceps. The electrosurgical HF generator can then comprise a measuring circuit for determining the resistance between the two clamping surfaces of the grasping forceps. With this measuring circuit, determining whether the clamping surfaces of the grasping forceps contact the tissue sufficiently can be achieved.

If the electrosurgical HF generator comprises a selector switch for connecting one clamping surface of the bipolar grasping forceps to the active output and for connecting the other clamping surface of the bipolar grasping forceps to the neutral output, then the operating mode of the HF generator can be switched by actuating the selecting switch from monopolar use to bipolar use; thereby increasing the range of applications for the HF generator. Preferably, the HF generator has a selector switch for separating the remaining electrodes i.e., the active electrode and the neutral electrode, from the generator circuit. This helps prevent accidents.

Preferably, the electrosurgical HF generator has a switch for separating the auxiliary neutral electrode from the generator circuit because not every operating situation requires an auxiliary neutral electrode to be applied to the tissue.

If the electrosurgical HF generator comprises a measuring circuit for determining the electric resistance between the neutral electrode and the auxiliary neutral electrode, then, before the actual treatment (i.e., before a surgeon cuts or coagulates the tissue to be treated), a determination as to whether both the neutral electrode and the auxiliary neutral electrode have been correctly applied to the tissue (i.e., they make sufficient contact therewith) can be made.

BRIEF DESCRIPTION OF THE DRAWINGS

Exemplary embodiments of the invention will now be described in greater detail with reference to the drawings, in which.

DETAILED DESCRIPTION

In the following description, the same reference signs are used for identical parts and parts acting in an identical manner.

Figure 1:
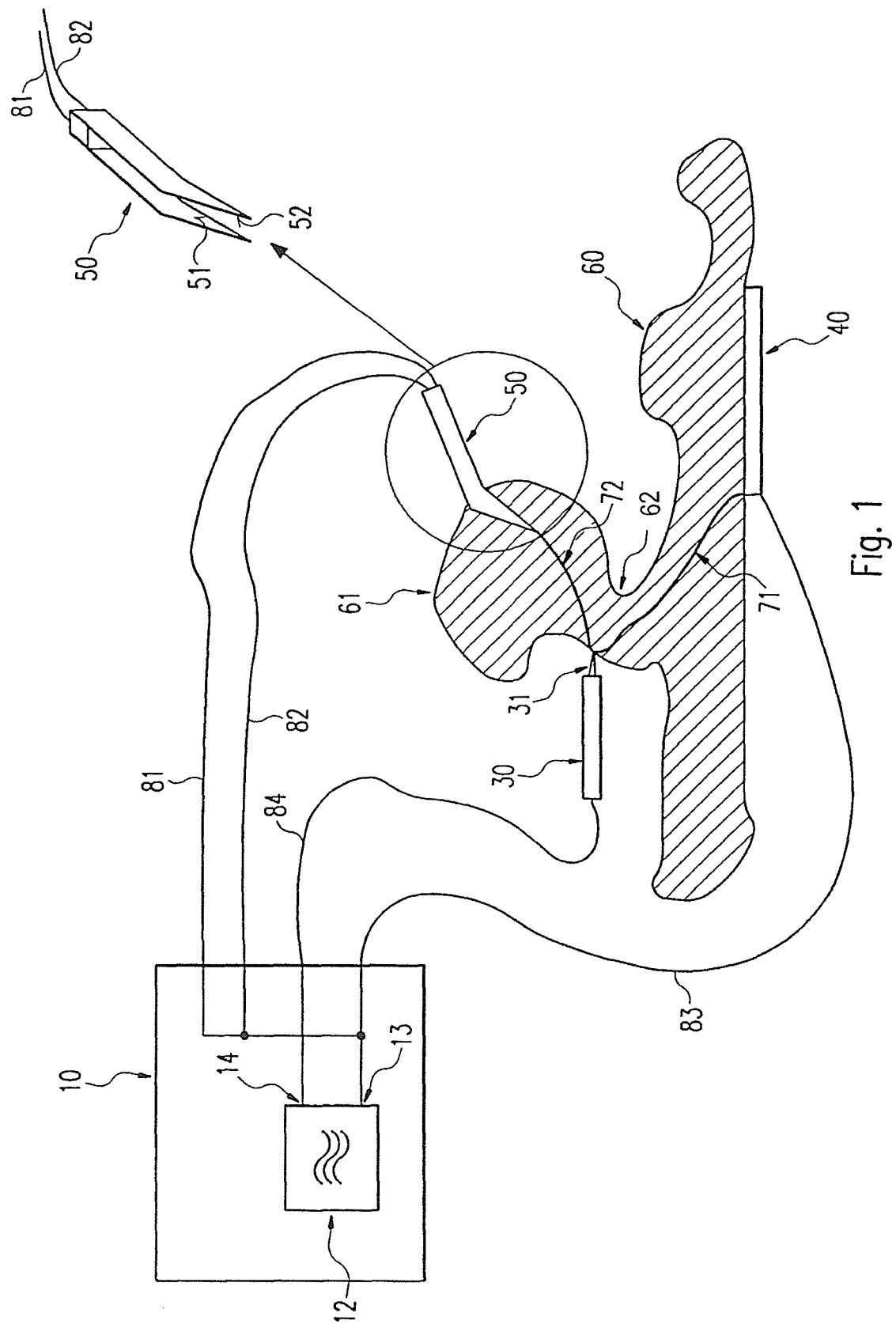
FIG. 1 shows a first embodiment of an electrosurgical HF generator disclosed herein.

The HF generator 10 in FIG. 1 comprises a generator circuit 12 with a neutral output 13 and an active output 14. The neutral output 13 is connected, via a line 83, to a neutral electrode 40 contacting tissue 60 over a large area. In addition, the neutral output 13 is connected, via lines 81, 82, to two clamping surfaces 51, 52 of a pair of bipolar grasping forceps 50, which serve as auxiliary neutral electrodes that contact a part 61 of the tissue 60 that is to be separated. The active output 14 is connected, via a line 84, to an active electrode 30 that is configured as a hand-piece and comprises an electrode tip 31. Using a switch (not shown), which can be configured as a foot switch or as a hand switch on the active electrode 30, a surgeon can close the circuit so that an HF current flows between the active output 14 and the neutral output 13 of the generator circuit 12. This HF current divides between two current paths 71, 72 through the tissue 60. The first current path 71 runs from the electrode tip 31 to the neutral electrode 40. The second current path 72 runs from the electrode tip 31 to the auxiliary neutral electrode, i.e. to the clamping surfaces 51, 52 of the bipolar grasping forceps 50. The current density along the first current path 71, via a tissue region 62 of narrowed cross-section, is reduced accordingly compared with monopolar electrosurgical treatment with an HF generator according to the prior art (i.e. a prior art generator without the clamping surfaces 51, 52 of the grasping forceps 50, which in the disclosed embodiments function as auxiliary neutral electrodes). The tissue regions that are not to be treated are accordingly heated less along the first current path 71, particularly in tissue region 62.

Figure 2:
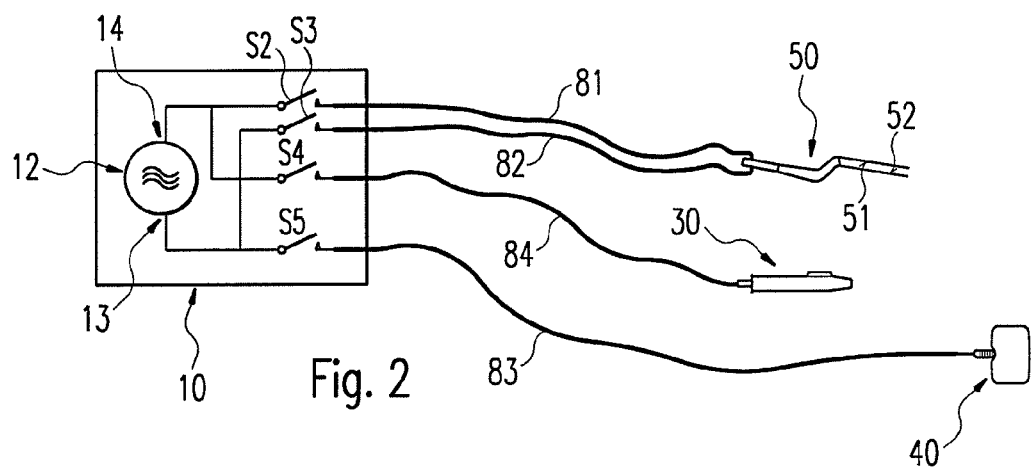
FIG. 2 shows a second embodiment of an electrosurgical HF generator.

The electrosurgical HF generator 10 according to FIG. 2 is similarly constructed to the generator of FIG. 1 except that it can be operated either in monopolar mode or in bipolar mode. For monopolar mode, switches S4 and S5 are closed (switches S2 and S3 remain in the open position), so that one neutral electrode 40 is connected to the neutral output 13 and one active electrode 30 is connected to the active output 14. Alternatively, switches S2 and S3 can be closed (S4 and S5 remain in the open position), so that one clamping surface 52 of a pair of bipolar grasping forceps 50 is connected, via a line 82, to the neutral output 13 and the other clamping surface 51 of the bipolar grasping forceps 50 is connected, via a line 81, to the active output 14. Consequently, the HF generator can be used with bipolar instruments when switches S2, S3 are closed.

Figure 3:
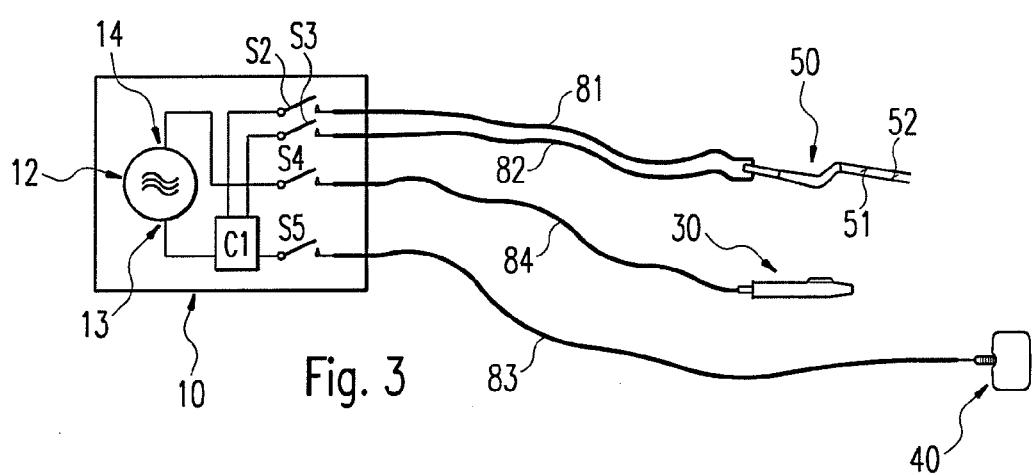
FIG. 3 shows a further embodiment of an electrosurgical HF generator.

The HF generator 10 according to FIG. 3 essentially corresponds to the HF generator of FIG. 1, with the following noted differences. With the switches S2, S3 and S5, the neutral electrode 40 and the clamping surfaces serving as auxiliary neutral electrodes 51, 52 of the bipolar grasping forceps 50 can be connected to the neutral output 13 of the generator circuit 12. The corresponding lines 81, 82, 83 from the neutral output 13 to the clamping surfaces 51, 52 and to the neutral electrode 40 are routed via a measuring circuit C1. The measuring circuit C1 determines the currents through the clamping surfaces 51, 52 and the current through the neutral electrode 40, as well as the ratio of said currents. If a measured value lies outside the corresponding previously set value range, then this is signalled to the surgeon, for example, with an indicator (not shown). The circuit C1 preferably measures the resistance between the neutral electrode 40 and the two clamping surfaces 51, 52 of the auxiliary neutral electrode before the actual electrosurgical treatment. If this resistance is above a previously determined limit value, then the switch S4 between the active electrode 30 and the active output 14 can be locked in an open position and/or a corresponding warning signal can be given to the surgeon (e.g., with an LED) to indicate that he should check the seating of the neutral electrode 40 and the auxiliary neutral electrode(s). If an auxiliary neutral electrode cannot be applied during an operation, the switches S2 and S3 remain open.

Figure 4:
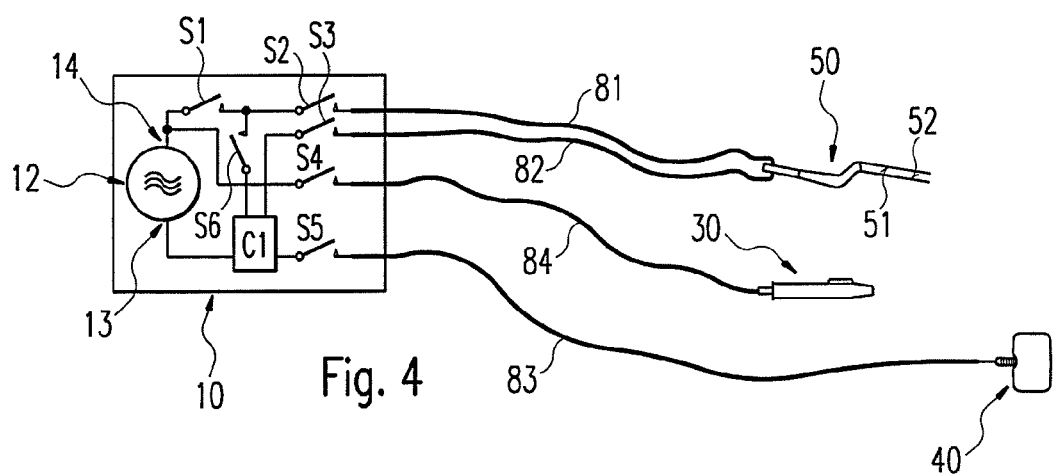
FIG. 4 shows an electrosurgical HF generator for monopolar and bipolar use.

The electrosurgical HF generator 10 in FIG. 4 comprises, like the electrosurgical generator in FIG. 3, a generator circuit 12 with a neutral output 13 and an active output 14, which can be connected, via a series of switches S1 to S6, to an active electrode 30 configured as a hand-piece or to a neutral electrode 40 and/or the clamping surfaces 51, 52 of a pair of bipolar grasping forceps 50. Switches S1 to S6 enable the electrodes to be connected to the active and neutral outputs 13, 14 so that both monopolar (with and without the auxiliary electrode(s)) and bipolar electrosurgical treatments can be carried out with the electrosurgical generator 10. For conventional monopolar electrosurgical treatment, only switches S4 and S5 are closed. The active electrode 30 is then connected to the active output 14 and the neutral electrode 40 is connected to the neutral output 13 of the generator circuit 12. If switches S2, S3 and S6 are also closed, the clamping surfaces 51, 52 of the bipolar grasping forceps 50 are also connected to the neutral output 13 of the generator circuit 12 and serve as an auxiliary neutral electrode. In this operating mode, using the measuring circuit C1 described above with reference to FIG. 3, the correct seating of the neutral electrode 40 and of the auxiliary neutral electrodes 51, 52 is monitored. If switches S4, S5 and S6 are opened and switches S1, S2 and S3 are closed, a clamping surface 52 of the bipolar grasping forceps 50 is connected to the neutral output 13 of the generator circuit 12 and the other clamping surface 51 is connected to the active output 14 of the generator circuit 12. With the selection switches Si to S6 in this setting, bipolar electrosurgical treatment can be carried out with the bipolar instrument 50 as usual. With the selection switches S1 to S6, the electrosurgical HF generator 10 according to FIG. 4 offers the possibility of carrying out monopolar electrosurgical treatment with the active electrode 30 and with the neutral electrode 40. In addition, clamping surfaces 51, 52 of a pair of bipolar grasping forceps 50 can be connected as auxiliary neutral electrodes. Alternatively, the electrosurgical HF generator 10 also enables bipolar electrosurgical treatment using the bipolar instrument 50. In this case, switches S1 to S6 are shown only symbolically. In order to prevent faulty operation, the switches S1 to S6 are preferably controlled via an operating mode selection element that is to be controlled by a surgeon.

The invention claimed is:

1. An electrosurgical high frequency (HF) system for treating biological tissue using an HF current, said electrosurgical HF system comprising:
   a generator circuit for generating the HF current, said generator circuit comprising an active output and a neutral output;

an instrument for treating the biological tissue using the HF current and connected to the active output;

a neutral electrode configured as a return pad and connected to the neutral output to create a first current path through the biological tissue between the instrument and the neutral electrode; and an auxiliary neutral electrode connected to the neutral output to create a second current path though the biological tissue between the instrument and the auxiliary neutral electrode, the auxiliary neutral electrode being configured as a clamping surface of a clamping instrument.

2. The electrosurgical HF system of claim 1, further comprising a measuring circuit that is configured to measure at least a ratio of HF current flowing through the first current path and through the second current path.

3. The electrosurgical HF system of claim 1, further comprising a measuring circuit that is configured to measure HF current flowing through the first current path and through the second current path.

4. The electrosurgical HF system of claim 1, further comprising a switch for separating the auxiliary neutral electrode from the generator circuit.

5. The electrosurgical HF system of claim 1, further comprising a measuring circuit that is configured to measure an electrical resistance between the neutral electrode and the auxiliary neutral electrode.

6. The electrosurgical HF system of claim 1, wherein the electrosurgical HF system is for cutting or coagulating the tissue.

7. The electrosurgical HF system of claim 1, wherein the auxiliary neutral electrode is connected in parallel to the neutral electrode.

8. The electrosurgical HF system of claim 1, wherein the neutral electrode is connected to the neutral output with a first wire and the auxiliary neutral electrode is connected to the neutral output with a second wire different than the first wire.

9. The electrosurgical HF system of claim 8, wherein the instrument is connected to the active output by a third wire different than the first and second wires.

10. The electrosurgical HF system of claim 1, wherein the auxiliary neutral electrode is not directly connected to the active output.

11. The electrosurgical HF system of claim 1, wherein the instrument for treating biological tissue is a monopolar instrument.

12. The electrosurgical HF system of claim 1, wherein the clamping instrument is a pair of grasping forceps.

13. The electrosurgical HF system of claim 12, wherein the grasping forceps are self-locking.

14. The electrosurgical HF system of claim 12, wherein the clamping surface comprises a first clamping surface and a second clamping surface, the first clamping surface having a first clamping surface electrode and the second clamping surface having a second clamping surface electrode, and wherein the first clamping surface electrode and second clamping surface electrode are connected to the neutral output by separate wires.

* * * * *